(12) United States Patent
Stadtler et al.

(10) Patent No.: US 11,202,583 B2
(45) Date of Patent: Dec. 21, 2021

(54) MAGNETIC RESONANCE GRADIENT ACCESSORY PROVIDING TAILORED GRADIENTS FOR DIFFUSION ENCODING

(71) Applicant: YALE UNIVERSITY, New Haven, CT (US)

(72) Inventors: Gigi Galiana Stadtler, New Haven, CT (US); Robert Todd Constable, Madison, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/784,437

(22) Filed: Feb. 7, 2020

(65) Prior Publication Data

US 2020/0253501 A1 Aug. 13, 2020

Related U.S. Application Data

(60) Provisional application No. 62/802,534, filed on Feb. 7, 2019.

(51) Int. Cl.
| | |
|---|---|
| *A61B 5/055* | (2006.01) |
| *G01R 33/3815* | (2006.01) |
| *G01R 33/385* | (2006.01) |
| *G01R 33/3875* | (2006.01) |

(52) U.S. Cl.
CPC .......... *A61B 5/055* (2013.01); *G01R 33/3815* (2013.01); *G01R 33/3852* (2013.01); *G01R 33/3875* (2013.01)

(58) Field of Classification Search
CPC ............ G01R 33/3815; G01R 33/3852; G01R 33/3875; A61B 5/055
See application file for complete search history.

(56) References Cited

U.S. PATENT DOCUMENTS

| | | | | |
|---|---|---|---|---|
| 5,311,134 | A | * | 5/1994 | Yamagata .......... G01R 33/3858 324/318 |
| 5,485,087 | A | * | 1/1996 | Morich ................ G01R 33/385 324/318 |
| 5,783,943 | A | * | 7/1998 | Mastandrea, Jr. ... G01R 33/385 324/318 |
| 5,786,692 | A | * | 7/1998 | Maier .............. G01R 33/56341 324/307 |

(Continued)

OTHER PUBLICATIONS

Agarwal, Harsh K. et al.. Optimal High b-Value for Diffusion Weighted MRI in Diagnosing High Risk Prostate Cancers in the Peripheral Zone, Journal of Magnetic Resonance Imaging, Jan. 2017, vol. 45, No. 1, pp. 125-131.

(Continued)

*Primary Examiner* — Dixomara Vargas
(74) *Attorney, Agent, or Firm* — Welsh Flaxman & Gitler, LLC

(57) ABSTRACT

A system includes a magnetic resonance gradient accessory within an MRI system. The MRI system includes a magnet housing, a superconducting magnet generating a magnet field B0 to which a patient is subjected, shim coils, RF coils, receiver coils, magnetic gradient coils, and a patient table. The magnetic resonance gradient accessory creates local magnetic gradient fields critical to image generation and provides for diffusion encoding of a specific body region.

16 Claims, 18 Drawing Sheets
(16 of 18 Drawing Sheet(s) Filed in Color)

(56) References Cited

U.S. PATENT DOCUMENTS

| | | | | | |
|---|---|---|---|---|---|
| 5,899,858 | A | * | 5/1999 | Muthupillai | G01R 33/56358 600/410 |
| 6,445,184 | B1 | * | 9/2002 | Tanttu | G01R 33/56341 324/307 |
| 6,777,936 | B2 | * | 8/2004 | Schaaf | G01R 33/385 324/318 |
| 6,864,683 | B2 | * | 3/2005 | Schuster | G01R 33/385 324/318 |
| 6,894,497 | B2 | * | 5/2005 | Renz | G01R 33/3854 324/318 |
| 6,969,991 | B2 | * | 11/2005 | Bammer | G01R 33/56341 324/307 |
| 7,250,765 | B2 | * | 7/2007 | Dietz | G01R 33/28 324/318 |
| 8,339,138 | B2 | * | 12/2012 | Parker | G01R 33/385 324/318 |
| 9,581,671 | B2 | * | 2/2017 | Dannels | G01R 33/56554 |
| 9,687,172 | B2 | * | 6/2017 | Bhat | G01R 33/56341 |
| 10,492,710 | B2 | * | 12/2019 | Wang | A61B 5/055 |
| 10,545,211 | B2 | * | 1/2020 | Harris | G01R 33/56509 |
| 10,866,293 | B2 | * | 12/2020 | O'Halloran | G01R 33/445 |
| 2008/0259560 | A1 | * | 10/2008 | Lvovsky | G01R 33/3856 361/689 |
| 2010/0102815 | A1 | * | 4/2010 | Parker | G01R 33/385 324/309 |
| 2012/0240385 | A1 | * | 9/2012 | Teklemariam | G01R 33/385 29/592.1 |
| 2013/0187649 | A1 | * | 7/2013 | Bhat | A61B 5/055 324/307 |
| 2014/0203809 | A1 | * | 7/2014 | Tanaka | G01R 33/3804 324/318 |
| 2015/0015253 | A1 | * | 1/2015 | Mori | G06T 7/30 324/309 |
| 2015/0241537 | A1 | * | 8/2015 | Dannels | G01R 33/56554 324/309 |
| 2015/0362570 | A1 | * | 12/2015 | Sakakura | G01R 33/4215 324/319 |
| 2016/0291112 | A1 | | 10/2016 | Constable | |
| 2017/0038444 | A1 | * | 2/2017 | Seeber | G01R 33/3858 |
| 2017/0123029 | A1 | * | 5/2017 | Bhat | G01R 33/5611 |
| 2017/0139023 | A1 | * | 5/2017 | Kusahara | G01R 33/4818 |
| 2017/0319098 | A1 | * | 11/2017 | Wang | A61B 5/055 |
| 2019/0004137 | A1 | * | 1/2019 | Harris | G01R 33/56572 |
| 2019/0025392 | A1 | * | 1/2019 | Chen | A61B 5/7267 |
| 2019/0033410 | A1 | * | 1/2019 | Ennis | G01R 33/561 |
| 2019/0128987 | A1 | * | 5/2019 | Feiweier | G01R 33/56341 |
| 2020/0049779 | A1 | * | 2/2020 | Overweg | G01R 33/56 |
| 2020/0379072 | A1 | * | 12/2020 | Basser | A61B 5/0044 |

OTHER PUBLICATIONS

Desouza, N.M. et al., Diffusion-weighted magnetic resonance imaging: a potential non-invasive marker of tumour aggressiveness in localized prostate cancer, Clinical Radiology (2008) 63, 774-782.
Wang, Haifeng et al., O-space with high resolution readouts outperforms radial imaging, Magnetic Resonance Imaging 37 (2017) 107-115.
Galiana, Gigi et al., The Role of Nonlinear Gradients in Parallel Imaging: A k-Space Based Analysis, Concepts in Magnetic Resonance Part A, vol. 40A(5) 253-267 (2012).
Galiana, Gigi et al., Spin Dephasing Under Nonlinear Gradients: Implications for Imaging and Field Mapping, Magnetic Resonance in Medicine 67:1120-1126 (2012).
Galiana, Gigi et al., Multiecho Acquisition of O-Space Data, Magnetic Resonance in Medicine 72:1648-1657 (2014).
Galiana, Gigi & Constable Todd R., Single Echo MRI, Jan. 2014 | vol. 9 | Issue 1 | e86008, pp. 1-6.
Kitajima Kazuhiro et al., Do apparent diffusion coefficient (ADC) values obtained using high b-values with a 3-T MRI correlate better than a transrectal ultrasound (TRUS)-guided biopsy with true Gleason scores obtained from radical prostatectomy specimens for patients with prostate cancer?, European Journal of Radiology 82 (2013) 1219-1226.
Liss Michael A et al. MRI-derived restriction spectrum imaging cellularity index is associated with high grade prostate cancer on radical prostatectomy specimens, Feb. 2015 | vol. 5 | Article 30, pp. 1-8.
Dispenza Nadine L. et al., Trajectory design of optimized repeating linear and nonlinear gradient encoding using a k-space point spread function metric, Proc. Intl. Soc. Mag. Reson. Med. 24 (2016), https://cds.ismrm.org/protected/16MPresentations/abstracts/3173.html.
Mueller-Lisse, Ullrich G., Everyman's prostate phantom: kiwi-fruit substitute for human prostates at magnetic resonance imaging, diffusion-weighted imaging and magnetic resonance spectroscopy, Eur Radiol (2017) 27:3362-3371.
Ong Wee L. et al. Transperineal biopsy prostate cancer detection in first biopsy and repeat biopsy after negative transrectal ultrasound-guided biopsy: the Victorian Transperineal Biopsy Collaboration experience, BJU Int 2015; 116: 568-576.
Shaish Hiram et al., The utility of quantitative ADC values for differentiating high-risk from low-risk prostate cancer: a systematic review and meta-analysis, Abdom Radiol (2017) 42:260-270.
Shin Toshitaka et al., Detection of prostate cancer using magnetic resonance imaging/ultrasonography image-fusion targeted biopsy in African-American men, BJU Int 2017; 120: 233-238.
Siddiqui Minhaj, M. et al., Comparison of MR/Ultrasound Fusion-Guided Biopsy With Ultrasound-Guided Biopsy for the Diagnosis of Prostate Cancer, JAMA. Jan. 27, 2015; 313(4): 390-397.
Stejskal O. E. & Tanner E. J., Spin Diffusion Measurements: Spin Echoes in the Presence of a Time-Dependent Field Gradient, J. Chem. Phys. 42, 288-292 (1965).
Stockmann Jason P. et al., O-Space Imaging: Highly Efficient Parallel Imaging Using Second-Order Nonlinear Fields as Encoding Gradients With No Phase Encoding, Magnetic Resonance in Medicine 64:447-456 (2010).
Stockmann Jason P. et al., In Vivo O-Space Imaging with a Dedicated 12cm Z2 Insert Coil on a Human 3T Scanner Using Phase Map Calibration, Magnetic Resonance in Medicine 69:444-455 (2013).
Tam Leo K. et al., Null Space Imaging: Nonlinear Magnetic Encoding Fields Designed Complementary to Receiver Coil Sensitivities for Improved Acceleration in Parallel Imaging, Magnetic Resonance in Medicine 68:1166-1175 (2012).
Tam Leo K. et al., Pseudo-Random Center Placement O-Space Imaging for Improved Incoherence Compressed Sensing Parallel MRI, Magnetic Resonance in Medicine 73:2212-2224 (2015).
Wang, Haifeng et al., Experimental O-Space Turbo Spin Echo Imaging, Magnetic Resonance in Medicine 75:1654-1661 (2016).
Wang, Haifeng et al., Fast Rotary Nonlinear Spatial Acquisition (FRONSAC) Imaging, Magnetic Resonance in Medicine 75:1154-1165 (2016).
Wang, Haifeng et al., Accelerate Single-Shot Data Acquisitions Using Compressed Sensing and Fronsac Imaging, 2015 IEEE, pp. 1252-1255.
Weinreb Jeffrey C. et al., PI-RADS Prostate Imaging—Reporting and Data System: 2015, Version 2, European Urology 69 (2016) 16-40.
White Nathan S., Diffusion-Weighted Imaging in Cancer: Physical Foundations and Applications of Restriction Spectrum Imaging, Cancer Res; 74(17) Sep. 1, 2014.
Yamin Ghiam, Voxel Level Radiologic-Pathologic Validation of Restriction Spectrum Imaging Cellularity Index with Gleason Grade in Prostate Cancer, Clin Cancer Res; 22(11) Jun. 1, 2016.

* cited by examiner

Fitting the diffusion curve to raw images yields the same ADC, whether diffusion encoding comes from nonlinear or linear gradients (1st row). Because the nonlinear gradient is stronger, it can use a shorter TE, leading to high signal (and SNR) in maps of S0, as shown in the 2nd row.

ADC maps simulated with actual field and geometry

Linear gradients, 40mT/m

Inside-out gradient
Closest approach

Ground truth

Offsetting the device reduces gradient strength but still provides large improvements in SNR
Linear gradients, 40mT/m
Inside-out gradient
Closest approach
Inside-out gradient
Offset 5cm
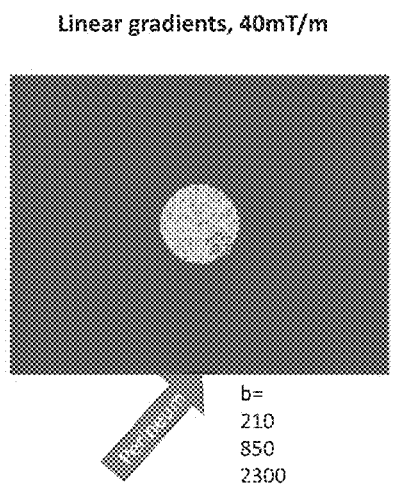
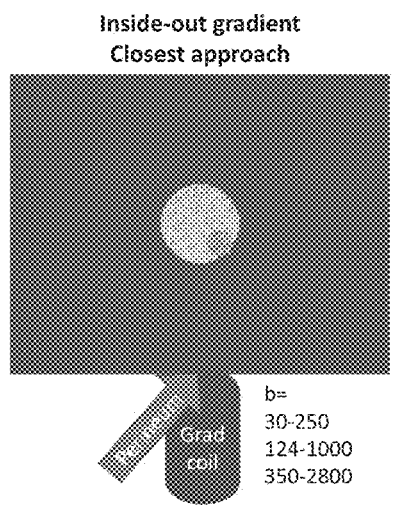
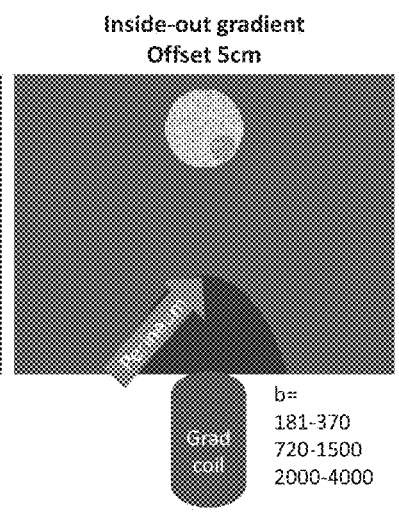
FIG. 13D
FIG. 13E
FIG.13 F Offset geometry also reduces dB/dt within the body Yes, stronger gradients will help a lot

MAGNETIC RESONANCE GRADIENT ACCESSORY PROVIDING TAILORED GRADIENTS FOR DIFFUSION ENCODING

CROSS REFERENCE TO RELATED APPLICATION

This application claims the benefit of U.S. Provisional Application Ser. No. 62/802,534, entitled "MAGNETIC RESONANCE GRADIENT ACCESSORY PROVIDING TAILORED GRADIENTS FOR DIFFUSION ENCODING," filed Feb. 7, 2019, which is incorporated herein by reference.

BACKGROUND OF THE INVENTION

1. Field of the Invention

The invention relates to magnetic resonance imaging (MRI). More particularly, the invention relates to magnetic resonance imaging using a magnetic resonance gradient generating accessory adapted for a specific body region, for example, the prostate.

2. Description of the Related Art

MRI, and particularly MRI employing diffusion weighted imaging (DWI), is the best imaging method for seeing prostate cancer. DWI uses the diffusion of water molecules to improve contrast in images generated via MRI. It is not only critical for spotting new cancers, but also for getting biopsies that actually sample the lesion, so that appropriate treatment can be pursued. However, though diffusion weighted MRI is very good at making healthy tissue look different from cancer, it suffers from extremely low signal overall, so images are very noisy with low resolution. Because of this poor image quality, biopsy hit rates, for example, in prostate treatment, are disappointingly low, and biopsies are often inconclusive.

The quality of diffusion weighted MRI is typically limited by the strength of the available magnetic gradient field. Weak gradients require a long time to encode diffusion, during which signal decay erodes signal-to-noise ratio (SNR) and contrast. However, the gradients used for diffusion are typically those designed for imaging and are built into the MRI system's body coil, which greatly limits their maximum strength. Imaging gradients need to be linear and unidirectional, which requires many cancellations/inefficiencies in the design. Imaging gradients are also expected to be uniform across a large cylindrical volume, increasing energy requirements which scale as $r^5$. Finally, imaging applications need gradients with fast ramping times, which also encourages design changes which reduce maximum amplitude.

When employing diffusion weighted MRI, cancer looks different from the healthy tissue as a result of the application of an uneven magnetic field, called a gradient, which is turned on for a period of time before the actual image is acquired. DWI provides the most sensitive and specific technique available to noninvasively detect lethal prostate cancer. Weinreb J C, Barentsz J O, Choyke P L, et al. PI-RADS Prostate Imaging—Reporting and Data System: 2015, Version 2. *Eur Urol.* 2016; 69(1):16-40. Shaish H, Kang S, Rosenkrantz A. The utility of quantitative ADC values for differentiating high-risk from low-risk prostate cancer: a systematic review and meta-analysis. *Abdom Radiol* (NY).42:260-270. deSouza N M, Riches S F, Vanas N J, et al. Diffusion-weighted magnetic resonance imaging: a potential non-invasive marker of tumour aggressiveness in localized prostate cancer. *Clin Radiol.* 2008; 63(7):774-782. Kitajima K, Takahashi S, Ueno Y, et al. Do apparent diffusion coefficient (ADC) values obtained using high b-values with a 3-T MRI correlate better than a transrectal ultrasound (TRUS)-guided biopsy with true Gleason scores obtained from radical prostatectomy specimens for patients with prostate cancer? *Eur J Radiol,* 2013; 82(8)1219-1226. Improved DWI would impact not only diagnosis, but also surgical planning, treatment monitoring, and especially biopsies, which currently have low hit rates and are often inconclusive. Siddiqui M M, Rais-Bahrami S, Turkbey B, et al. Comparison of MR/ultrasound fusion-guided biopsy with ultrasound-guided biopsy for the diagnosis of prostate cancer. *JAMA.* 2015; 313(4):390-397. Shin T, Smyth T B, Ukimura O, et al. Detection of prostate cancer using magnetic resonance imaging/ultrasonography image-fusion targeted biopsy in African-American men. *BJU international.* 2017; 120(2):233-238. Ong W L, Weerakoon M, Huang S, et al. Transperineal biopsy prostate cancer detection in first biopsy and repeat biopsy after negative transrectal ultrasound-guided biopsy: the Victorian Transperineal Biopsy Collaboration experience. *BJU international.* 2015; 116(4):568-576. However, DWI is plagued by extremely low signal because the weak gradients designed for imaging require long echo times to achieve sufficient encoding.

DWI and its quantitative counterpart apparent diffusion coefficient (ADC) mapping, are the most definitive way to noninvasively detect peripheral zone tumors, which make up ~75% of cases. Weinreb J C, Barentsz J O, Choyke P L, et al. PI-RADS Prostate Imaging—Reporting and Data System: 2015, Version 2. *Eur Urol.* 2016; 69(1):16-40. DWI has consistently been shown to reflect Gleason score, so it specifically improves detection of clinically significant, i.e. potentially lethal, prostate cancer. Shaish H, Kang S, Rosenkrantz A. The utility of quantitative ADC values for differentiating high-risk from low-risk prostate cancer: a systematic review and meta-analysis. *Abdom Radiol* (NY). 42:260-270. deSouza NM, Riches S F, Vanas N J, et al. Diffusion-weighted magnetic resonance imaging: a potential non-invasive marker of tumour aggressiveness in localized prostate cancer. *Clin Radiol.* 2008; 63(7):774-782. Kitajima K, Takahashi S, Ueno Y, et al. Do apparent diffusion coefficient (ADC) values obtained using high b-values with a 3-T MRI correlate better than a transrectal ultrasound (TRUS)-guided biopsy with true Gleason scores obtained from radical prostatectomy specimens for patients with prostate cancer? *Eur J Radiol.* 2013; 82(8):1219-1226.2-4 However, prostate DWI, as currently practiced, suffers from low SNR and limited contrast. This in turn severely limits resolution, reproducibility, and inter-reader agreement, leading to inaccurate biopsies and grading, which directly impact clinical outcomes. Therefore, a dramatic improvement in DWI image quality would lead to earlier definitive detection of potentially lethal prostate cancer, which is the key to addressing the overarching challenge of reducing lethal prostate cancer in high risk populations.

Current mechanisms for creating gradients in MRI are too weak and not ideal for DWI. In order to generate sufficient diffusion contrast for the differentiation of healthy and cancerous tissue, current gradients must be turned on for a very long time, during which the MRI signal rapidly disappears. By the time the actual image is being acquired, very little signal is left and the resulting images are poor.

With the foregoing in mind, current methods of prostate biopsy are shockingly crude, sampling a predetermined template of 12 cores and hoping that one hits the cancer, a particularly ineffective strategy for small pre-metastatic lesions. More sophisticated methods incorporate MR images and fuse them with real-time ultrasound guidance, yet these approaches are limited by the underlying MR image quality. Siddiqui M M, Rais-Bahrami S, Turkbey B, et al. Comparison of MR/ultrasound fusion-guided biopsy with ultrasound-guided biopsy for the diagnosis of prostate cancer. JAMA. 2015; 313(4):390-397. Improved biopsy guidance appears particularly important for high risk groups, like African American men, where MRI quadrupled the biopsy detection rate of clinically significant prostate cancer (53% vs 12%) and increased efficiency (one potentially lethal cancer per 13 vs 82 cores). Shin T, Smyth T B, Ukimura O, et al. Detection of prostate cancer using magnetic resonance imaging/ultrasonography image-fusion targeted biopsy in African-American men. BJU international. 2017; 120(2): 233-238. Even still, the hit rate on repeat biopsies is often just slightly lower than hit rates on initial biopsies (36% vs 53%), which suggests massive room for improvement. Ong W L, Weerakoon M, Huang S, et al. Transperineal biopsy prostate cancer detection in first biopsy and repeat biopsy after negative transrectal ultrasound-guided biopsy: the Victorian Transperineal Biopsy Collaboration experience. BJU international. 2015; 116(4):568-576. Better DWI of prostate is the key to improving this critical step of diagnostic workup.

Referring to FIGS. 1a-1c, while FIG. 1a shows good signal and resolution, FIGS. 1b and 1b show the very poor image quality typical of prostate ADC and DWI. Using typical gradient strengths, diffusion weighting requires long time intervals, during which signal and contrast decay. This leads to poor image quality and high inter-reader variability, with serious clinical repercussions.

In the patient shown in FIG. 1b, the ADC map was extremely noisy in the entire peripheral zone. Due to susceptibility effects associated with the longtime intervals, a highly experienced radiologist deemed the signal void (yellow arrows) to be part artifact, making it PI-RADS (Prostate Imaging Reporting and Data System) 3, equivocal for the presence of clinically significant cancer. A second reading by another highly experienced radiologist read the entire void as a region of restricted diffusion and assigned it as PI-RADS 5, highly suspicious of malignancy. Simulating an image with higher b-value (a factor reflecting the strength and timing of the gradients used to generate diffusion-weighted images), that is, higher diffusion weighting, further confirmed the second assessment (FIG. 1c), though this approach is often limited by SNR in the original images. Ultimately, the second assessment was substantiated by a biopsy yielding multiple cores of prostatic adenocarcinoma, which prompted immediate treatment. This case exemplifies how low image quality can lead to ambiguous readings and seriously impact clinical outcomes. Furthermore, it hints at the promise of greater diffusion weighting, which is not typically achievable given current SNR levels. Agarwal H K, Mertan F V, Sankineni S, et al. Optimal high b-value for diffusion weighted MRI in diagnosing high risk prostate cancers in the peripheral zone. Journal of magnetic resonance imaging: JMRI. 2017; 45(1):125-131. In addition to standard protocols, the future of many exciting developments in prostate MRI (such as Restricted Spectrum Imaging, previously supported by the PCRP (Prostate Cancer Research Program)) hinge on better quality DWI. White N S, McDonald C, Farid N, et al. Diffusion-weighted imaging in cancer: physical foundations and applications of restriction spectrum imaging. Cancer research. 2014; 74(17): 4638-4652. Liss M A, White N S, Parsons J K, et al. MRI-Derived Restriction Spectrum Imaging Cellularity Index is Associated with High Grade Prostate Cancer on Radical Prostatectomy Specimens. Front Oncol. 2015; 5:30. Yamin G, Schenker-Ahmed N M, Shabaik A, et al. Voxel Level Radiologic-Pathologic Validation of Restriction Spectrum Imaging Cellularity Index with Gleason Grade in Prostate Cancer. Clin Cancer Res. 2016; 22(11):2668-2674.

SUMMARY OF THE INVENTION

According to a first aspect there may be provided a system including a magnetic resonance gradient accessory within a conventional MRI system. The MRI system comprises a magnet housing, a superconducting magnet generating a magnet field B0 to which a patient is subjected, shim coils, RF coils, receiver coils, magnetic gradient coils, and a patient table. The magnetic resonance gradient accessory creates local magnetic gradient fields critical to image generation, and the magnetic resonance gradient accessory provides for diffusion encoding of a specific body region of a patient.

In some embodiments the system includes measurement circuitry producing data used to reconstruct images displayed on a display.

In some embodiments the magnetic resonance gradient accessory includes a magnetic field generating gradient coil.

In some embodiments the magnetic field generating gradient coil is composed of a set of electromagnets embedded in a housing of the magnetic resonance gradient accessory.

In some embodiments the magnetic field generating gradient coil comprises hollow wire conductors allowing for the passage of fluid therethrough for superior heat dissipation.

In some embodiments the magnetic field generating gradient coil is centered in the housing.

In some embodiments the housing is secured to the patient table.

In some embodiments the magnetic field generating gradient coil is electrically coupled to a gradient amplifier providing the electrical current necessary to energize the magnetic field generating gradient coil so as to distort the main magnetic field in predetermined locations to thereby creating magnetic gradients.

In some embodiments the magnetic resonance gradient accessory is 10 cm long.

In some embodiments use of the magnetic resonance gradient accessory achieves >400 mT/m in the region of interest.

In a further aspect a magnetic resonance gradient accessory for use within an MRI system comprises a magnet housing, a superconducting magnet generating a magnet field B0 to which a patient is subjected, shim coils, RF coils, receiver coils, magnetic gradient coils, and a patient table. The magnetic resonance gradient accessory includes a housing and a magnetic field generating gradient coil creating local magnetic gradient fields critical to image generation and providing for diffusion encoding of a specific body region.

Additional advantages of the embodiments will be set forth in part in the description which follows, and in part will be understood from the description, or may be learned by practice of the invention. The advantages will be realized and attained by means of the elements and combinations particularly pointed out in the appended claims.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIGS. 13A-13I are schematic representations of ADC maps. FIGS. 13A-13C show ADC maps simulated with actual field and geometry, FIGS. 13D-13F show that over-setting the magnetic resonance gradient accessory reduces gradient strength but still provides large improvements in SNR, and FIGS. 13G-13I show that offset geometry also reduces dB/dt within the body.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring now to the various drawings, the present invention improves MRI implemented using DWI through the application of a magnetic resonance gradient accessory 10 within an MRI system 100.

Before proceeding with the detailed description of the present invention, it is appreciated that MRI uses spatially-varying magnetic fields, termed gradients, in order to spatially localize signals. Fundamentally, magnetic resonance imaging differs from spectroscopy through the use of gradients that assign different frequency codes to separate spatial regions in the area to be imaged. The Larmor precession equation states that the frequency of the RF signal applied in MRI processing be proportional to the magnetic field intensity.

Figure 1:
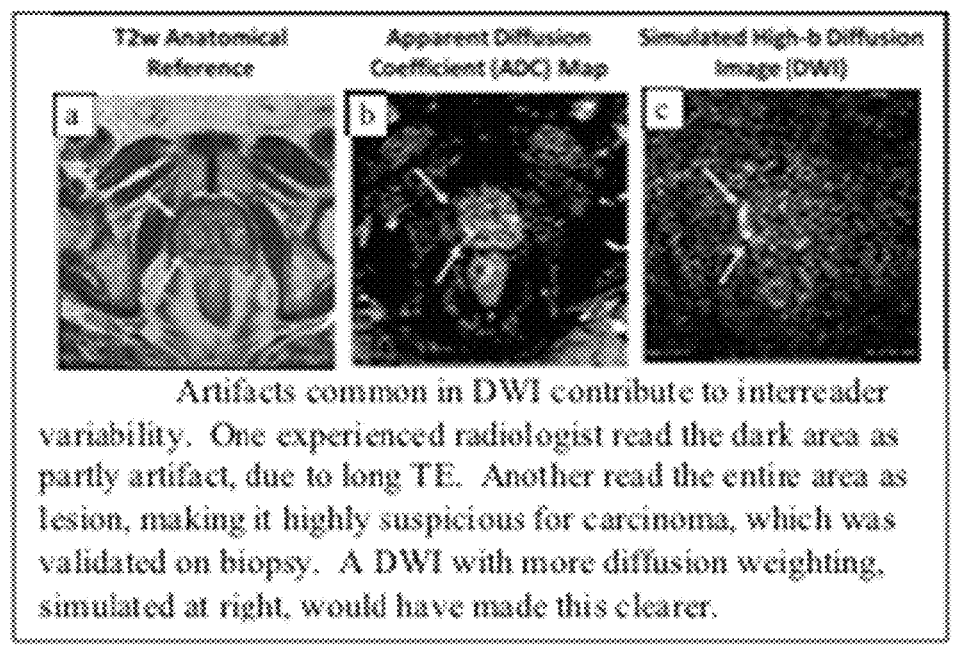
FIGS. 1a, 1b, and 1c (cumulatively FIG. 1) illustrate the need for enhanced signal to noise ratio in prostate DWI. The T2 (transverse relaxation time) weighted anatomical image (FIG. 1a) shows good signal and resolution, but there is little contrast between healthy tissue and lesion. The map of apparent diffusion coefficient (FIG. 1b) shows good contrast at the lesion, but has poor spatial resolution and signal. The third panel (FIG. 1c) simulates how this lesion could have been more apparent on an image with higher diffusion weighting (high b-value). With standard gradient amplitudes, high b-values require long echo times, which reduce signal.
Figure 2:
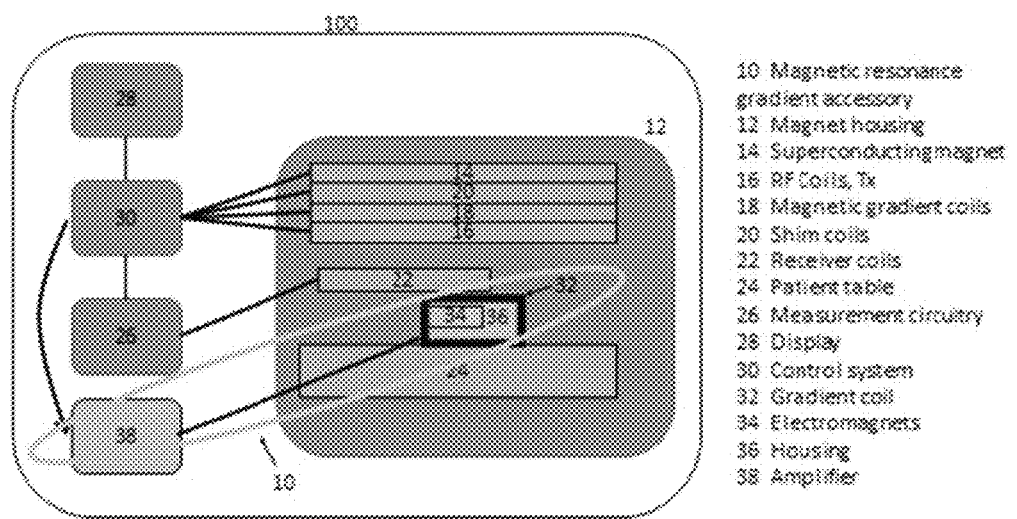
FIG. 2 shows a schematic of a standard MRI system including the magnetic resonance gradient accessory of the present invention.

With reference to FIG. 2, the imaging techniques of the present invention are intended for application within an MRI system 100. As is well appreciated by those skilled in the art, a superconducting magnet 14 of the MRI system 100 applies a spatially uniform and temporally constant main $B_0$ magnetic field. Further, excitation of nuclear spin magnetization within the examination volume of the magnetic housing 12 is applied by RF coils 16. More particular, the RF coils 16 apply a radio frequency pulse sequence, the $B_1$ field, which is superimposed perpendicular to the $B_0$ field at an appropriate proton resonant frequency.

Figure 14:
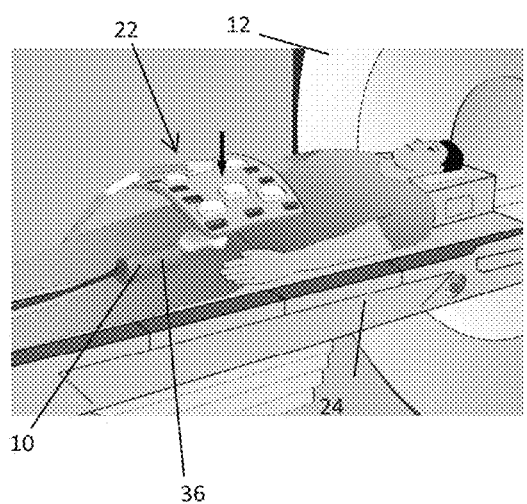
FIG. 14 is a perspective view showing the magnetic resonance gradient accessory as used in accordance with the present invention. The positioning of the device and the relative geometry of the scanner patient and receiver coils is shown.
Figure 15:
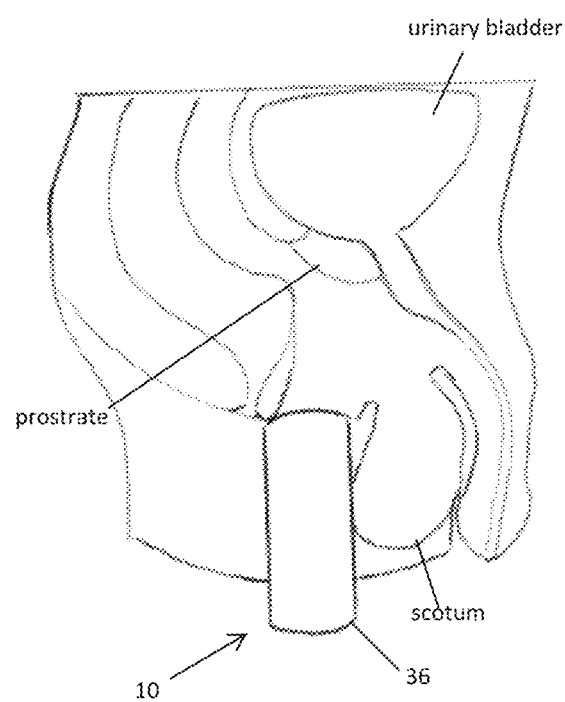
FIG. 15 is a detailed sectional view showing positioning of the magnetic resonance gradient accessory placed externally posterior to the genitalia and anterior to the anus, which yields close proximity to the prostate.

These more traditional components of the MRI system 100 are combined with a plurality of magnetic gradient coils 18 that apply magnetic gradient fields to the examination volume of the magnetic housing 12. The magnetic gradient fields facilitate spatial encoding of the nuclear spin magnetization. Conventional MRI systems employ magnetic gradient coils 18 that are positioned about the central cavity defined by the magnetic housing 12. However, and in accordance with the present invention localized gradients are generated by the magnetic resonance gradient accessory 10 that is positioned adjacent to the body region being studied. In accordance with a disclosed embodiment, and as used in imaging of the prostate, the magnetic resonance gradient accessory 10 is placed externally, posterior to the genitalia and anterior to the anus, which yields close proximity to the prostate (see FIGS. 14 and 15). Through the provision of a dedicated local coil in the form of the magnetic resonance gradient accessory 10 it is possible to greatly increase the available diffusion gradient strength for a given amplifier strength (by 10-fold in preliminary designs). Therefore, the magnetic resonance gradient accessory 10, a local gradient coil, generates a gradient in the magnetic field aimed at maximizing dBz/ds over the target region for the purpose of efficient diffusion encoding. This field need not be linear, unidirectional, or rapidly switchable.

During MRI procedures, pulse sequences composed of magnetic gradient fields (applied by the magnetic gradient coils 18 and/or the magnetic resonance gradient accessory 10) and radio frequency fields (applied by the RF coils 16 in a traditional manner) are applied to a targeted subject (such as a live patient) while subject to the temporally constant main $B_0$ magnetic field (applied by the superconducting magnetic 14) to generate magnetic resonance signals, which are detected, stored and processed to reconstruct spectra and images of the object. These procedures determine the characteristics of the reconstructed spectra and images such as location and orientation in the targeted subject, dimensions, resolution, signal-to-noise ratio, and contrast. The operator of the magnetic resonance device typically selects the appropriate sequence, and adjusts and optimizes its parameters for the particular application.

As briefly explained above, a schematic illustration of the MRI system 100 in accordance with the present invention is shown with reference to FIG. 2. As shown, the MRI system 100 includes a traditional magnet housing 12, a superconducting magnet 14 generating the magnet field $B_0$ to which the patient is subjected, shim coils 20, RF coils 16, receiver coils 22, and a patient table 24. The MRI system 100 also includes traditional magnetic gradient coils 18 and the magnetic resonance gradient accessory 10 creating the local magnetic gradient fields critical to the image generation in accordance with the present invention as well as traditional linear magnetic gradient fields. It is further appreciated the concepts present in the inventors' earlier U.S. Patent Application Publication No. 2016/0291112, entitled "SINGLE-ECHO IMAGING WITH NONLINEAR MAGNETIC GRADIENTS," which is incorporated herein by reference, could be applied in conjunction with the present invention.

As is well known in the art, the superconducting magnet 14 produces a substantially uniform magnetic $B_0$ field within its design field of view (FOV). This $B_0$ field is directed along the positive Z-axis. As for the gradient coils 18 and the magnetic resonance gradient accessory 10, the present MRI system 100 may employ a plurality of such gradient coils in such orientations necessary to generate the desired magnetic gradient field. As such, the magnetic resonance gradient accessory 10 can be applied alone or in conjunction with standard gradient coils 18 to generate diffusion encoding.

The MRI system 100 also includes measurement circuitry 26 producing data used to reconstruct images displayed on a display 28. Preferably, the application of control signals is achieved via a control system 30 linked to the various operational components of the MRI system 100 under the control of an operator of the MRI system 100. In accordance with a preferred embodiment, the control system 30 would switch the magnetic resonance gradient accessory 10 on and off in coordination with other components to generate diffusion encoding within an imaging scan, as appreciated by those skilled in the art.

Considering now the specifics of the magnetic resonance gradient accessory 10 in accordance with the present invention, the magnetic resonance gradient accessory 10 provides for diffusion encoding of a specific body region, for example, the prostate, in a manner that delivers a much stronger gradient and requires less time for diffusion encoding. The magnetic resonance gradient accessory 10 includes a magnetic field generating gradient coil 32 composed of a set of electromagnets 34 embedded in a housing 36 of the magnetic resonance gradient accessory 10. In accordance with a preferred embodiment, the magnetic resonance gradient accessory 10 is made with gradient coil 32 composed of hollow wire conductors for superior heat dissipation using simple chilled water (or other fluid) passing through the hollow wire conductors. Cooling mechanisms such as this limit the maximum gradient temperature so that it can be in direct contact with the patient, facilitating placement of the accessory to achieve maximum gradient over the targeted anatomy. The gradient coil 32 is centered in the housing 36 to minimize mechanical forces and coupling. The gradient coil 32 is held in place within the housing 36 by scaffolding (not shown) and the housing 36 is secured to the patient table 24 in a manner ensuring a symmetric location of the gradient coil 32 and restraining any residual movement. While a preferred construction of the magnetic resonance gradient accessory is disclosed herein, it is appreciated the construction may be varied to suit specific needs without departing from the spirit of the present invention. The magnetic field generating gradient coil 32 is electrically coupled to a gradient amplifier 38 providing the electrical current necessary to energize the magnetic field generating gradient coil 32 so as to distort the main magnetic field in predetermined locations to thereby creating magnetic gradients as desired in accordance with the present invention. The gradient amplifier 38 is under the control of the control system 30.

In accordance with a preferred embodiment, the gradient is controlled by simple trigger pulses that prescribe flat top gradient waveforms, like those applied in first generation O-Space experiments. Stockmann J P, Ciris P A, Galiana G, Tam L, Constable R T. O-Space imaging: Highly efficient parallel imaging using second-order nonlinear fields as encoding gradients with no phase encoding. *Magnetic Resonance in Medicine.* 2010; 64(2):447-456. Stockmann J P G, G., Tam L, Juchem C, Nixon T W, Constable R T. In vivo O-Space imaging with a dedicated 12 cm Z2 insert coil on a human 3T scanner using phase map calibration. *Magn Reson Med.* 2013; 69(2):444-455. Tam L K, Galiana G, Stockmann J P, Tagare H, Peters D C, Constable R T. Pseudo-random center placement O-space imaging for improved incoherence compressed sensing parallel MRI. *Magn Reson Med.* 2014. Galiana G, Peters D, Tam L, Constable R T. Multiecho acquisition of O-space data. *Magn Reson Med.* 2014; 72(6):1648-1657. Wang H, Tam L, Kopanoglu E, Peters D, Constable R T, Galiana G. Experimental O-Space Turbo Spin Echo Imaging. *Magnetic Resonance in Medicine.* 2015; Accepted. Wang H, Tam L, Kopanoglu E, Peters D, Constable R T, Galiana G. O-Space with high resolution readouts outperforms radial imaging. *Magnetic Resonance in Medicine.* 2017; 37(April):107-115. Stockmann J P, Galiana G, Tam L, Juchem C, Nixon T W, Constable R T. In vivo O-Space imaging with a dedicated 12 cm Z2 insert coil on a human 3T scanner using phase map calibration. *Magn Reson Med.* 2013; 69(2):444-455. Using this approach, both waveform design and sequence modification are trivial, requiring only the addition of a few trigger pulses. More sophisticated in-house software with dynamic waveform control is also available and could be applied if needed, and direct control via the controller 30 is also possible.

Figure 3:
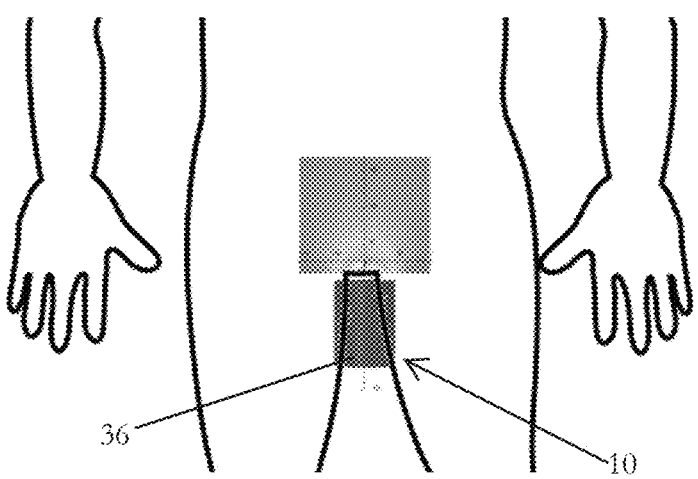
FIG. 3 shows a schematic positioning of one implementation of this invention for diffusion weighted imaging of prostate. The generated magnetic field creates a strong gradient across the prostate, 6-10 cm from the perineal surface, even though it produces very little field or gradient across the rest of the anatomy.

The magnetic resonance gradient accessory 10 (as shown in detail in FIG. 3) is a 10 cm long, narrow and single-sided design that can be pressed against the perineum to achieve close proximity to the prostate, even in heavy patients, while remaining compatible with typical body and spine receiver arrays. Positioning is external (not transrectal) to improve patient comfort and compliance. That is, and in contrast a typical volumetric gradient design where the hardware encircles the patient/anatomy, the magnetic resonance gradient accessory 10 is structured to be positioned simply adjacent to the patient/anatomy. FIG. 3 shows a design schematic with an overlay of the field generated by the magnetic resonance gradient accessory 10. As such, the housing 36 of the magnetic resonance gradient accessory 10 may take a variety of configurations so long as it is properly sized for positioning adjacent the anatomical feature requiring imaging and generating the desired gradient. For example, an as explained above, the exemplary magnetic resonance gradient accessory 10 would be relatively small in size and exhibit a largest dimension of approximately 10 cm. In particular, and in accordance with a disclosed embodiment, the magnetic resonance gradient accessory 10 is placed externally, posterior to the genitalia and anterior to the anus, which yields close proximity to the prostate for imaging thereof (see FIGS. 14 and 15). With imaging of the prostate in mind, and with reference to FIG. 14, the receiver coils 22 are positioned adjacent the area under study at a position above the patient in a manner that is well known to those skilled in the art.

Figure 4:
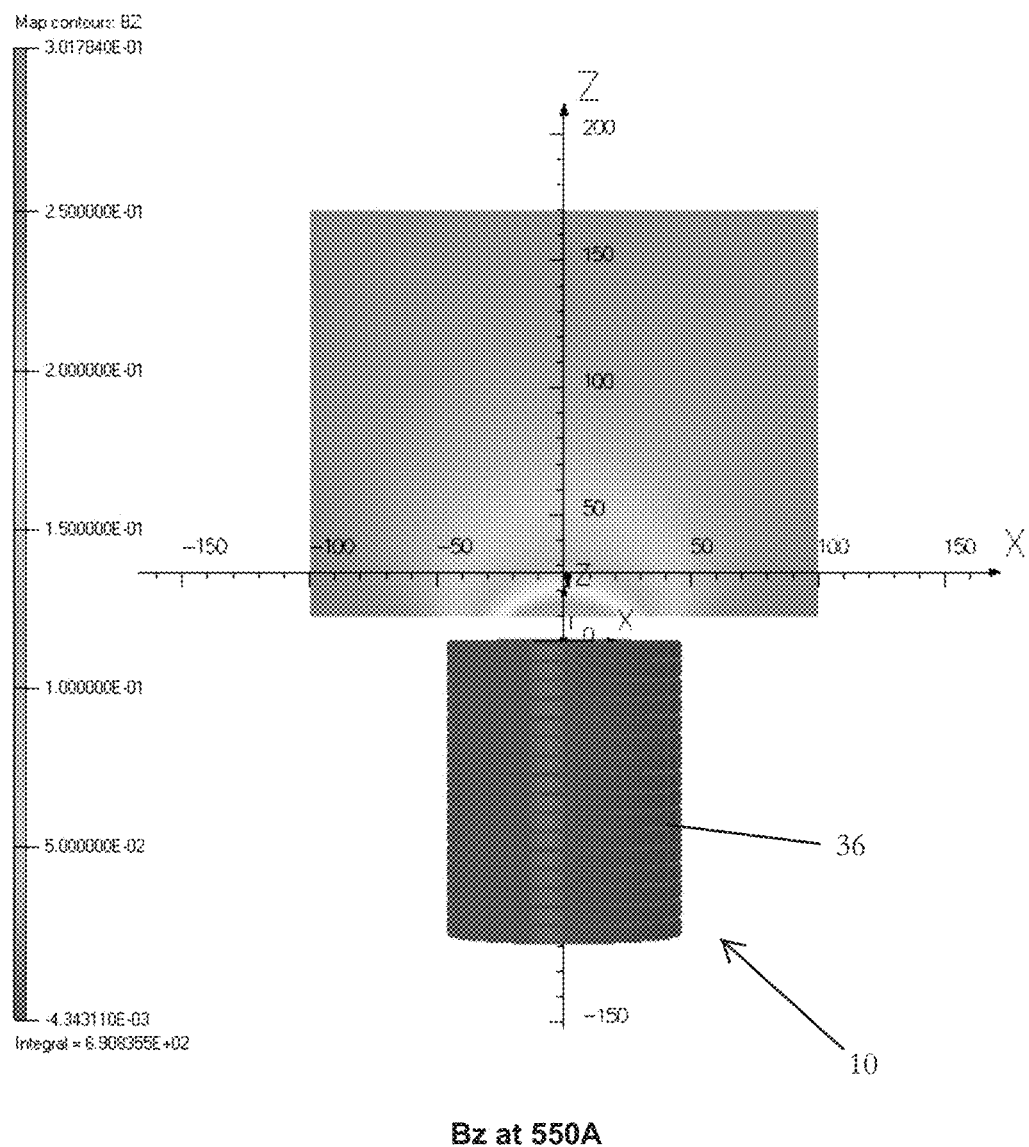
FIG. 4 shows in greater detail, the magnetic field generated by the magnetic resonance gradient accessory based upon the implementation described in FIG. 3.
Figure 5:
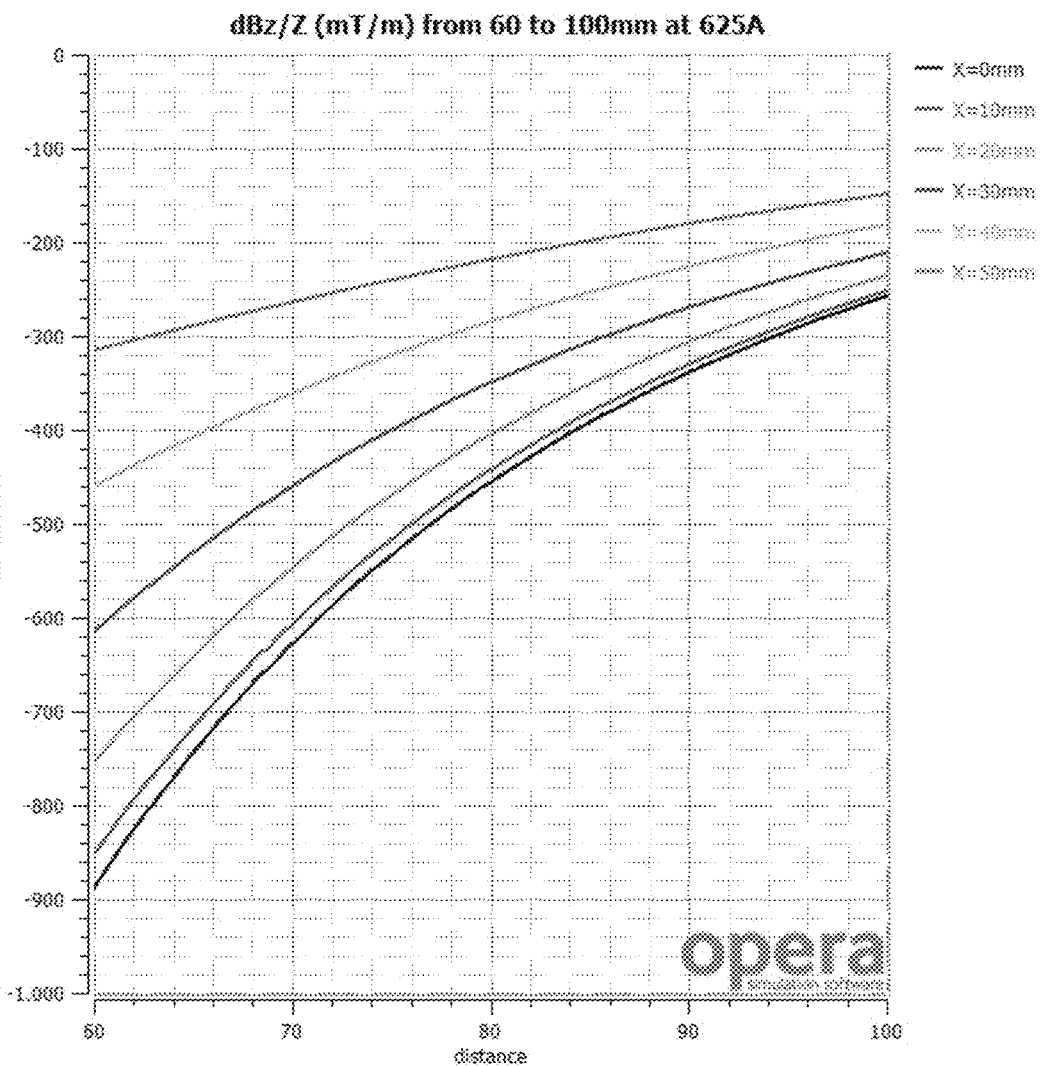
FIG. 5 plots the gradient of the magnetic field as a function of position in the z-direction (i.e., head-foot direction of patient for positioning shown in FIG. 3. The prostate is approximately a 4 cm sphere located 6-10 cm from the edge of the magnetic resonance gradient accessory, so the gradient in the region of interest is primarily characterized by the black, red, and green curves.

Referring to FIG. 4, most of the gradient field generated by the magnetic resonance gradient accessory 10 is Bz and the strongest direction of variance is along the z-direction, i.e. the head-foot direction of the patient, which is also the direction of static magnetic field 14. FIG. 5 plots the gradient as a function of z-position for various radial positions. Because a typical prostate is only on the order of 4 cm in diameter, the lines for x=0, x=10 and x=20 are the most relevant, with gradients averaging 450 mT/m. While most scanners deliver 40 mT/m for diffusion encoding, the magnetic resonance gradient accessory 10 delivers an average of ~450 mT/m over the prostate (60-100 mm from perineal surface), as shown in the plot for various radial locations. As stronger gradients impart diffusion encoding in a shorter echo time (TE), with large SNR gains, implementation of magnetic resonance gradient accessory 10 offers vast improvements over currently available systems.

Through the use of the magnetic resonance gradient accessory 10 a 6× increase in signal strength and a 3× increase in contrast are realized. The increases in signal strength and contrast transform image quality and make cancers much easier to spot. The magnetic resonance gradient accessory 10, therefore, improves the imaging and biopsy of prostate cancers, so that doctors always know what they're dealing with and can prescribe treatment accordingly.

In particular, considering that MRI is recognized as the most cost-effective and logical step following elevated PSA, and diffusion weighted MRI is considered the most informative image of the MRI protocol, it has been shown that in high risk groups, like African American men, MRI can quadruple the biopsy detection rate of clinically significant prostate cancer (53% vs 12%) with greater efficiency (one potentially lethal cancer per 13 vs 82 cores). The better images enabled by the magnetic resonance gradient accessory 10 will increase this further, to ultimately reduce the number of lethal prostate cancers in high risk groups, such as African Americans and Veterans.

As briefly explained above, the magnetic resonance gradient accessory 10, which is specifically adapted for DWI of specific body region, for example, for DWI of prostate, delivers high diffusion weighting at much shorter echo times, thereby boosting signal strength by up to 6× and contrast to noise (CNR) by 3×. Some of this gain can in turn be traded for better resolution or increased contrast, ultimately transforming the image quality of prostate DWI. Because the magnetic resonance gradient accessory 10 is implemented as a removable accessory, it could be quickly adopted into clinical practice in conjunction with any scanner, regardless of manufacturer, field strength, or bore size. It is also portable enough to share across different scanners within a hospital.

Figure 6:
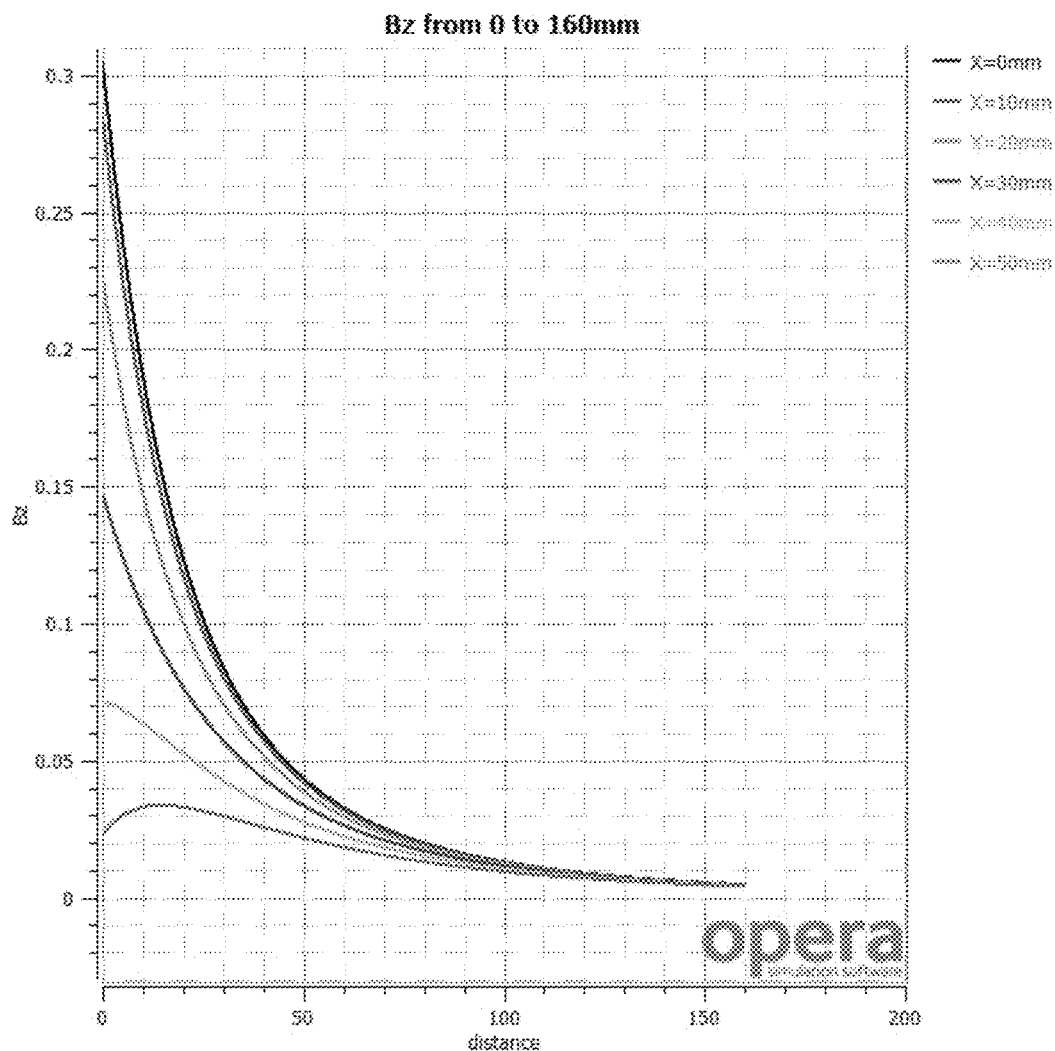
FIG. 6 shows a more quantitative representation of the field across a larger region.
Figure 7:
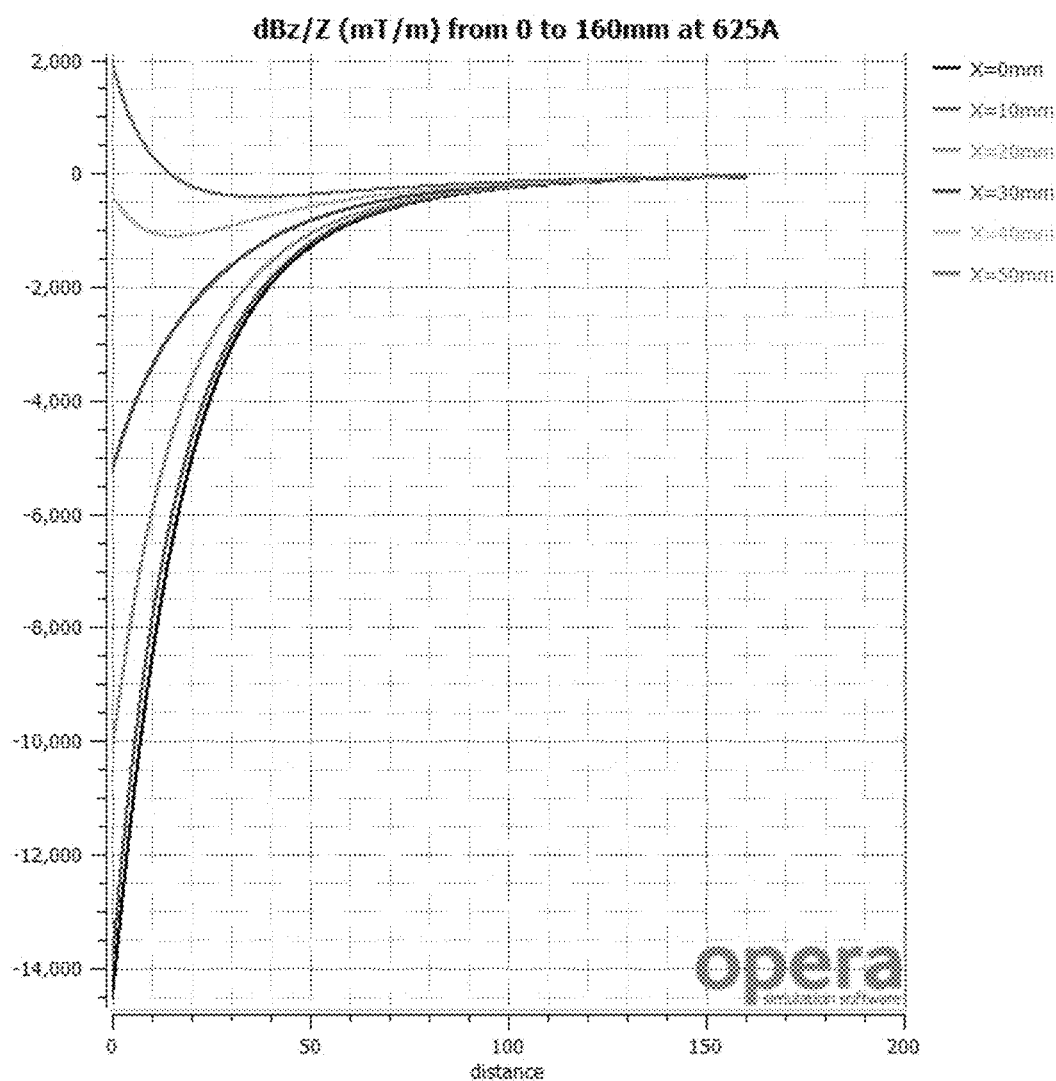
FIG. 7 shows a more quantitative representation of the gradient across a larger region.

The magnetic resonance gradient accessory 10 in accordance with the present invention is constructed to exhibit operating characteristics resulting in rapid and widespread impact on prostate imaging for its ability to improve not only detection, but also biopsy and grading (for example, see FIGS. 6 and 7). Furthermore, the magnetic resonance gradient accessory 10 is a relatively portable and affordable accessory that is compatible with any MRI scanner, and it is externally placed for patient comfort.

As briefly discussed above, the present invention provides a magnetic resonance gradient accessory 10 specifically designed for DWI of prostate. As implementation of the magnetic resonance gradient accessory 10 abandons typical gradient requirements on linearity, directionality, active volume, and rapid switching, the use of magnetic resonance gradient accessory 10 achieves >400 mT/m in the region of interest. Moreover, the magnetic resonance gradient accessory 10 has the potential to be implemented as an accessory compatible with any scanner, encouraging rapid adoption in practice.

Figure 12:
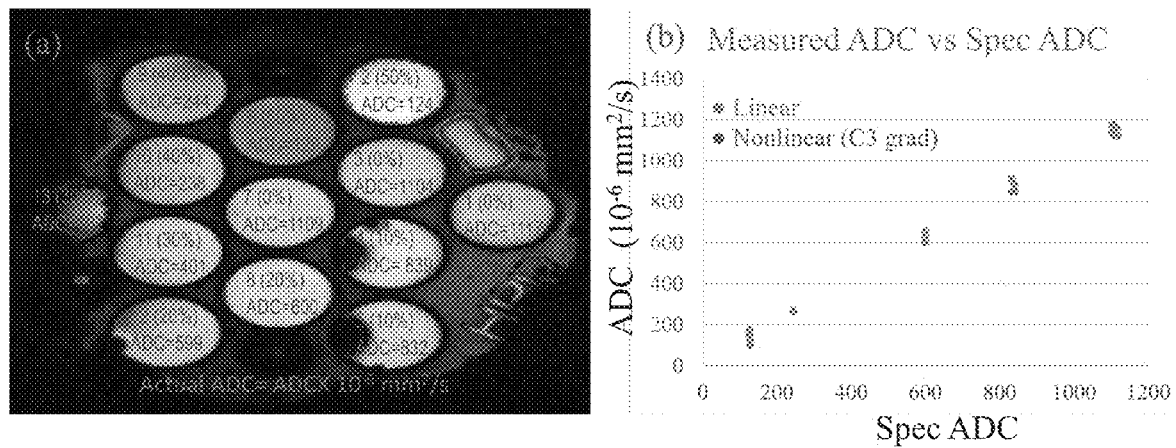
FIG. 12 shows graphical data relating to use with linear and nonlinear fields.

The following simulations show the likely impact of the gradients created by the dedicated magnetic resonance gradient accessory 10, including improvements in SNR, CNR and higher b-value imaging. In addition, experiments on phantoms show that diffusion weighting with nonlinear gradients is feasible and produces ADC maps and DW images in agreement with those from conventional gradients (see FIG. 12).

Preliminary Data: Simulations

Simulations were performed in Matlab assuming equal T2* between prostate cancer and healthy peripheral zone tissue (32 ms as measured at 3T in 3 patients) and D=0.36E−3 and 0.70E−3 for healthy and cancerous prostate tissue, respectively. Experiments were performed on a phantom of kiwi embedded in agarose gel. Both linear and nonlinear fields were mapped by a series of gradient echo images, and the resulting field maps were used to generate maps of gradient and b-value for each experiment. The signal from each voxel was fit to a monoexponential using b-values appropriate to that voxel, and those parameters were used to scale DWI images to a uniform diffusion weighting.

Results

Figure 4A:
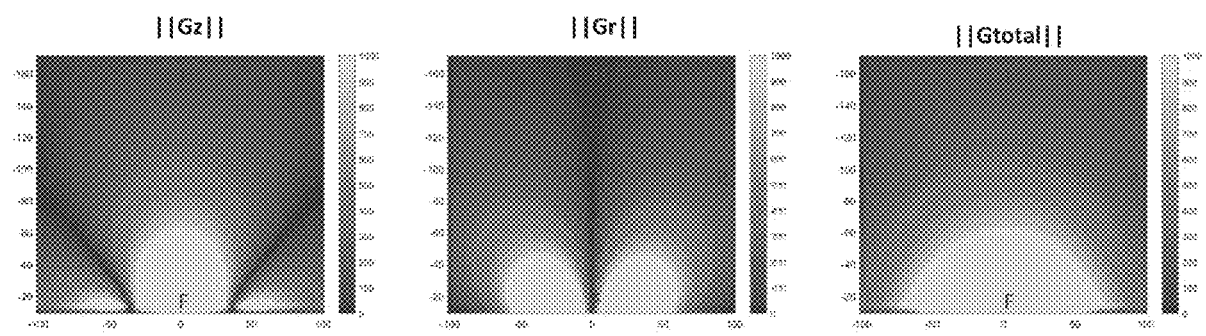
FIG. 4A shows the magnetic field generated in the xz plane.

FIG. 4 shows a schematic of the magnetic resonance gradient accessory 10 and the gradient ($dB_z/dz$) the magnetic resonance gradient accessory 10 achieves across the prostate, which was found to be 6-10 cm from the perineal surface according to MR images. Further, FIG. 4A shows the gradient field of the prostate in the xz plane as achieved through the use of the magnetic resonance gradient accessory 10. The gradient is designed to be centered in the bore, which minimizes forces and coupling, and it can be controlled by simple trigger pulses in the pulse sequence. For patient comfort and safety, the device has a radius of 5 cm and is water cooled to a maximum temperature of 43 C.

Figure 8:
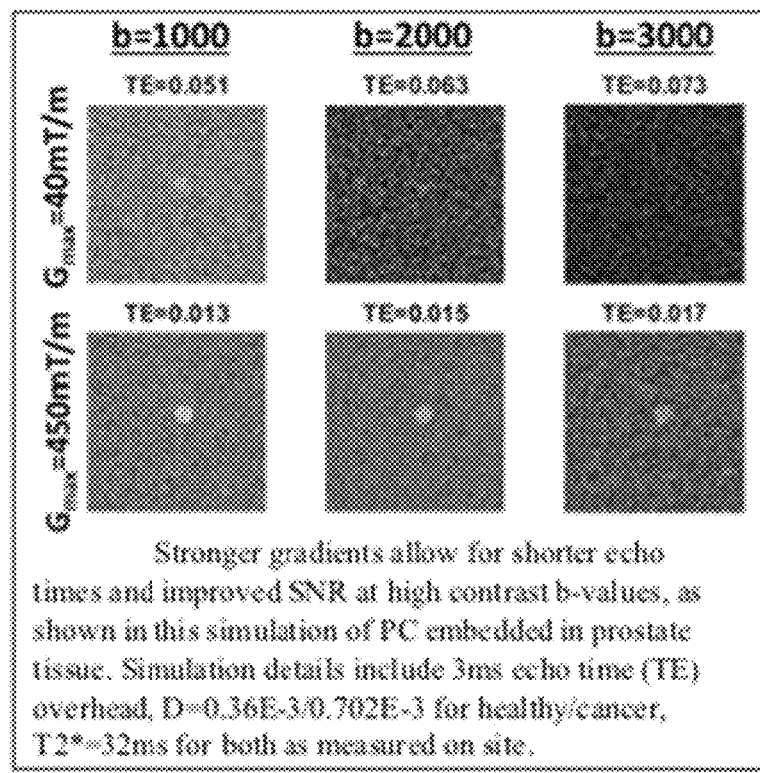
FIG. 8 shows simulations of the anticipated image quality for different b-values assuming a maximum available gradient of 40 mT/m (top row) and 450 mT/m (bottom row). The simulation of PC (prostate cancer) embedded in prostrate tissue. shows stronger gradients allow for shorter echo times and SNR (Signal-To-Noise) at high contrast b-values. The simulation details include 3 ms echo time (TE) overhead, D=0.36E−3/0.702E−3 for healthy/cancer, T2*=32 ms for both as measured on site.

FIG. 8 shows a simulation of the potential image improvements. Each column shows a low SNR simulation of a circle of prostate cancer embedded in healthy prostate tissue. As is typical of clinical scans, b=1000 is considered the upper limit of routinely achievable contrast, and even in these images SNR can be very low. As tested, the clinical protocol actually acquires images at b=800 and mathematically scales them to higher diffusion weighting, though this is known to reduce some sensitivity. Higher weighting can be achieved in far shorter diffusion encoding time (with less SNR loss) using the gradient strengths achieved in our preliminary design. Furthermore, at the same noise level, it becomes feasible to explore still higher b-values while maintaining adequate SNR.

Figure 9:
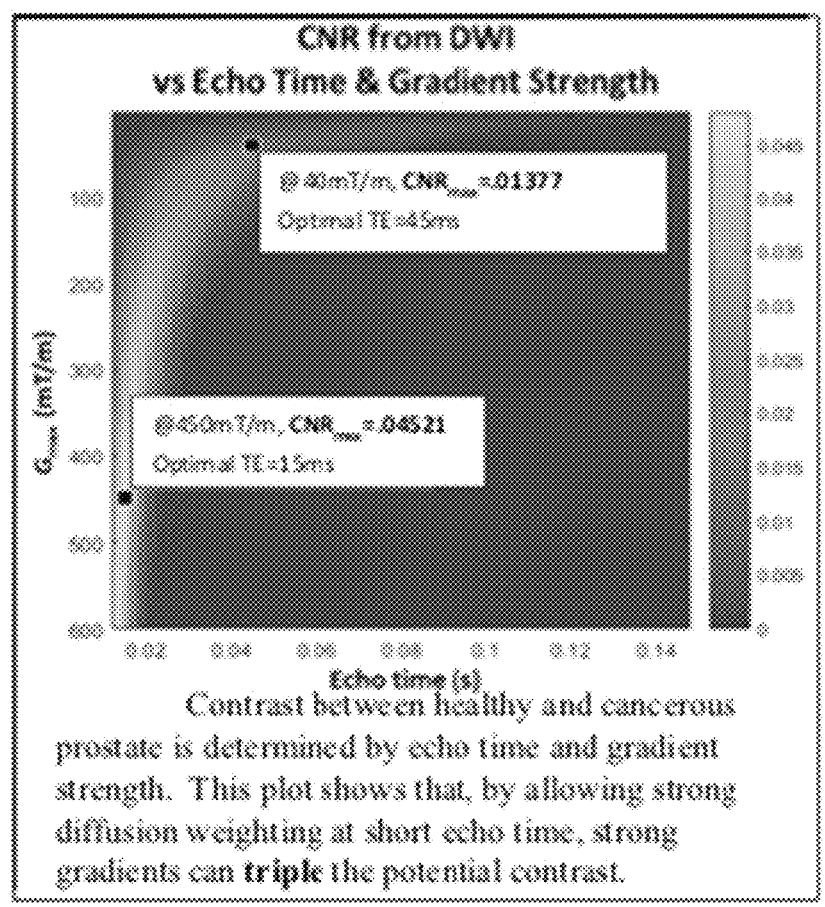
FIG. 9 shows a generalized simulation of the achievable contrast to noise ratio between prostate and cancer (color scale) for any gradient strength (y-axis) and echo time (x-axis). With weaker gradients, increasing b-value requires longer echo time, which robs the contrast that would be achievable with pure diffusion weighting.

To look more generally at the achievable contrast, FIG. 9 shows, for any combination of echo time (x-axis) and maximum gradient amplitude (y-axis), the contrast to noise ratio between prostate and prostate cancer (color scale). At 40 mT/m, the most widely available gradient strength for body imaging systems, the best contrast is achieved around 50 ms, which corresponds to b~1000 s/mm$^2$. At 450 mT/m, as achieved by the proposed hardware, much higher CNR is possible, encoded in less than 20 ms with far less signal loss. These simulations suggest a tripling of contrast is possible with the proposed hardware.

Preliminary Data: Experiments

One key to achieving an order of magnitude increase in gradient strength is accepting nonlinearity in the field, which provides nonuniform diffusion weighting across the image. Due to applicant's longstanding interest in nonlinear gradients, applicant was able to show initial feasibility of this approach with an existing nonlinear gradient coil. Galiana G, Stockmann J P, Tam L, Peters D, Tagare H, Constable R T. The role of nonlinear gradients in parallel imaging: A k-space based analysis. *Concepts in Magnetic Resonance Part A*. 40A(5):253-267. Stockmann J P, Ciris P A, Galiana G, Tam L, Constable R T. O-Space imaging: Highly efficient parallel imaging using second-order nonlinear fields as encoding gradients with no phase encoding. *Magnetic Resonance in Medicine*. 2010; 64(2):447-456. Galiana G, Stockmann J P, Tam L, Todd Constable R. Spin dephasing under nonlinear gradients: Implications for imaging and field mapping. *Magnetic Resonance in Medicine*. 2011. Tam L K, Stockmann J P, Galiana G, Constable R T. Null Space Imaging: Nonlinear Magnetic Encoding Fields Designed Complementary to Receiver Coil Sensitivities for Improved Acceleration in Parallel Imaging. *Magnetic Resonance in Medicine*. 2011; 68(4): 1166-75. Stockmann J P G, G., Tam L, Juchem C, Nixon T W, Constable R T. In vivo O-Space imaging with a dedicated 12 cm Z2 insert coil on a human 3T scanner using phase map calibration. *Magn Reson Med*. 2013; 69(2):444-455. Tam L K, Galiana G, Stockmann J P, Tagare H, Peters DC, Constable R T. Pseudo-random center placement O-space imaging for improved incoherence compressed sensing parallel MRI. *Magn Reson Med*. 2014. Galiana G, Constable R T. Single echo MRI. *PLoS One*. 2014;9(1). Galiana G, Peters D, Tam L, Constable R T. Multiecho acquisition of O-space data. *Magn Reson Med*. 2014; 72(6):1648-1657. Wang H, Tam L, Kopanoglu E, Peters D, Constable R T, Galiana G. Experimental O-Space Turbo Spin Echo Imaging. *Magnetic Resonance in Medicine*. 2015; Accepted. Wang H, Constable R T, Galiana G. Accelerated Single-Shot Data Acquisitions Using Compressed Sensing and FRONSAC Imaging. *Proceedings of the IEEE International Symposium on Biomedical Imaging*. 2015:483. Wang H, Tam L K, Constable R T, Galiana G. Fast rotary nonlinear spatial acquisition (FRONSAC) imaging. *Magn Reson Med*. 2016; 75(3):1154-1165. Luedicke N, Tagare H, Galiana G, Constable R T. Trajectory design of optimized repeating linear and nonlinear gradient encoding using a k-space point spread function metric. Paper presented at: ISMRM Annual Meeting 2016; Singapore. Wang H, Tam L, Kopanoglu E, Peters D, Constable R T, Galiana G. O-Space with high resolution readouts outperforms radial imaging. *Magnetic Resonance in Medicine*. 2017; 37(April): 107-115.

These experiments encoded diffusion using a field in the shape of $Bz(x,y)=x^3-2xy^2$, (aka, a C3 shape) and they imaged a kiwi embedded in agarose, which has been noted as an excellent phantom for DWI of prostate. Mueller-Lisse U G, Murer S, Mueller-Lisse U L, Kuhn M, Scheidler J, Scherr M. Everyman's prostate phantom: kiwi-fruit substitute for human prostates at magnetic resonance imaging, diffusion-weighted imaging and magnetic resonance spectroscopy. *Eur Radiol*. 2017; 27(8):3362-3371. These results show that mapping, compensation, and data analyses developed in our previous work directly apply to DWI. DWI encoded with nonlinear gradients is entirely consistent with the standard images acquired using linear gradients.

Moreover, though these experiments do not use gradients optimized for DWI and employ ~half the amplifier current, DWI with nonlinear gradients required far less encoding time for comparable diffusion weighting. This already led to a doubling in SNR, which can be seen more quantitatively in FIG. 10. This is because traditional linear gradients are inherently inefficient due to the many cancellations needed to achieve linearity over a large region.

Figure 11:
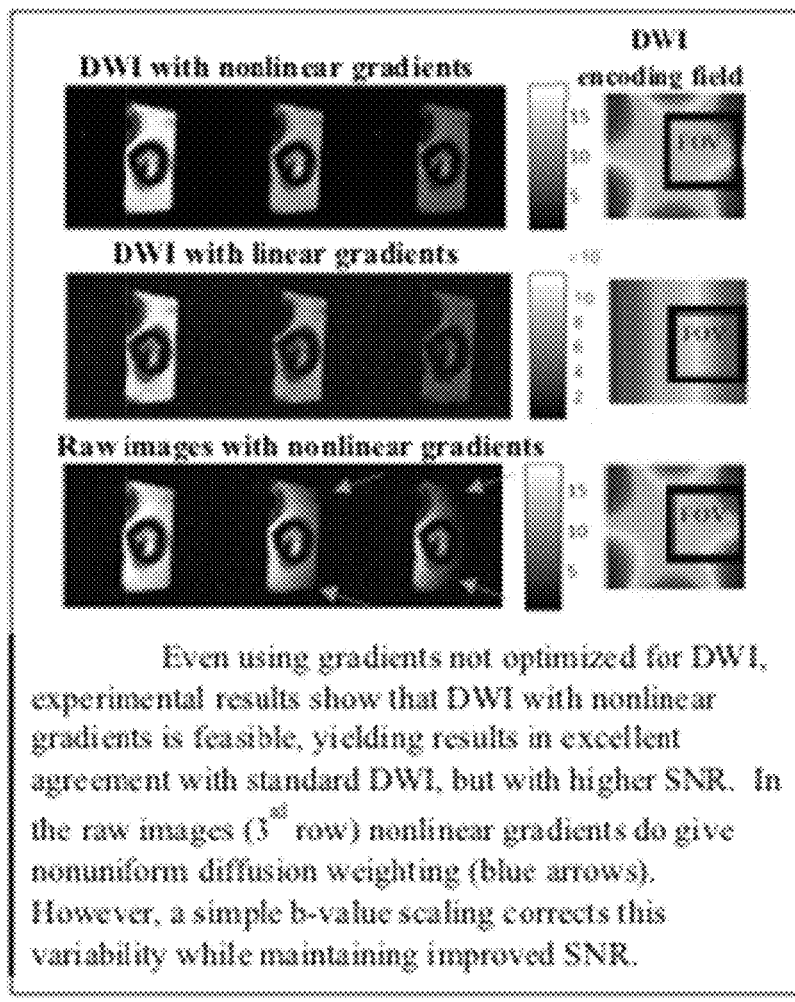
FIG. 11 shows phantom experiments demonstrating that properly corrected diffusion images from experiments with linear and nonlinear fields are equivalent. The raw images using nonlinear gradients have stronger gradients in certain regions, which leads to greater diffusion weighting, as shown in blue arrows. However, a simple correction for the spatially varying b-value is easily implemented.

Referring to FIG. 11, in the raw images acquired with nonlinear gradients (3rd row), one can see the spatial non-uniformity in diffusion weighting (blue arrows). However, a simple b-value scaling corrects this variability while maintaining improved SNR (1st row). Scaling to unmeasured b-values is already standard in clinical practice, and the only difference here is that the measured b-values are specific to each voxel. However, because of the improved SNR, this scaling is more reliable.

Implementation of the present magnetic resonance gradient accessory 10 requires some preliminary characterization following installation. In accordance with the present invention, a successful DWI sequence will require two different mappings, a detailed map of the static field used for diffusion weighting and a map of residual eddy current fields present during the image encoding. Methods for each of these have been tested and perfected in other nonlinear gradient projects. Stockmann J P, Ciris P A, Galiana G, Tam L, Constable R T. O-Space imaging: Highly efficient parallel imaging using second-order nonlinear fields as encoding gradients with no phase encoding. *Magnetic Resonance in Medicine*. 2010; 64(2):447-456. Wang H, Tam L K, Constable R T, Galiana G. Fast rotary nonlinear spatial acquisition (FRONSAC) imaging. *Magn Reson Med*. 2016; 75(3):1154-1165.

Figure 10:
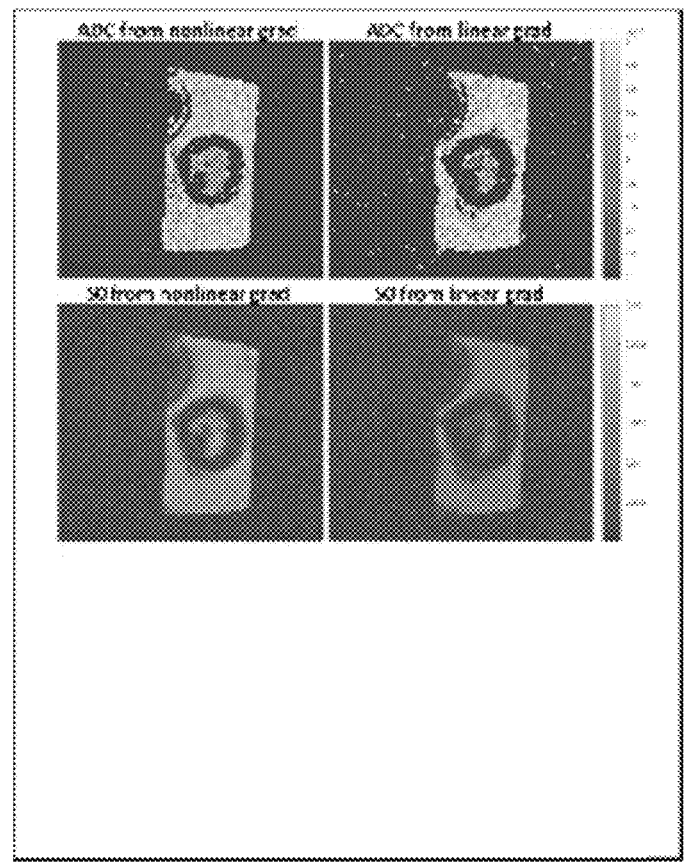
FIG. 10 shows phantom experiments demonstrating that apparent diffusion coefficients calculated from experiments with linear and nonlinear fields are equivalent. Those with nonlinear gradients achieve a higher SNR due to shorter echo time. Fitting the diffusion curve to raw images yields the same ADC, whether diffusion encoding comes from nonlinear or linear gradients (1st row). Because the nonlinear gradient is stronger, it can use a shorter TE, leading to high signal (and SNR) in maps of S0, as shown in the 2nd row.

FIG. 10 shows results calculating $S_0$ (MR signal at baseline) and ADC for each pixel using preliminary data using a nonlinear C3 gradient on a kiwi phantom. These are compared to similar results using a linear x-gradient. Notably, even existing nonlinear gradients running at about half the current, show significantly stronger local gradients than what can be achieved with the linear gradients, thus requiring a shorter TE (33 ms vs 60 ms). As expected, a significant improvement is seen in SNR, quantified in $S_0$ which shows about a doubling of signal.

Figure 13A:
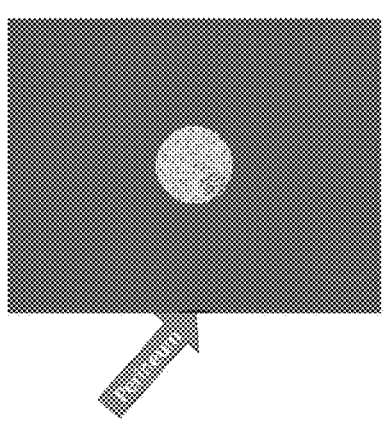
Figure 13B:
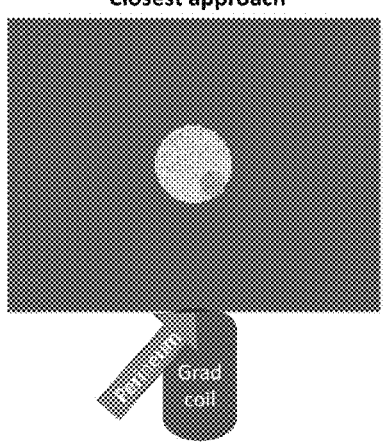
Figure 13C:
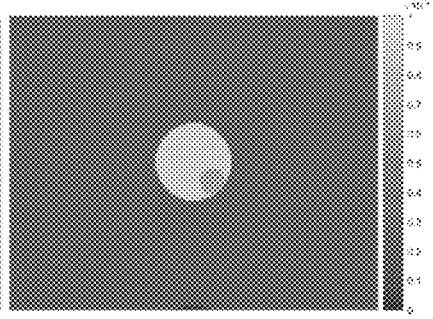
Figures 13G, 13H, 13I:
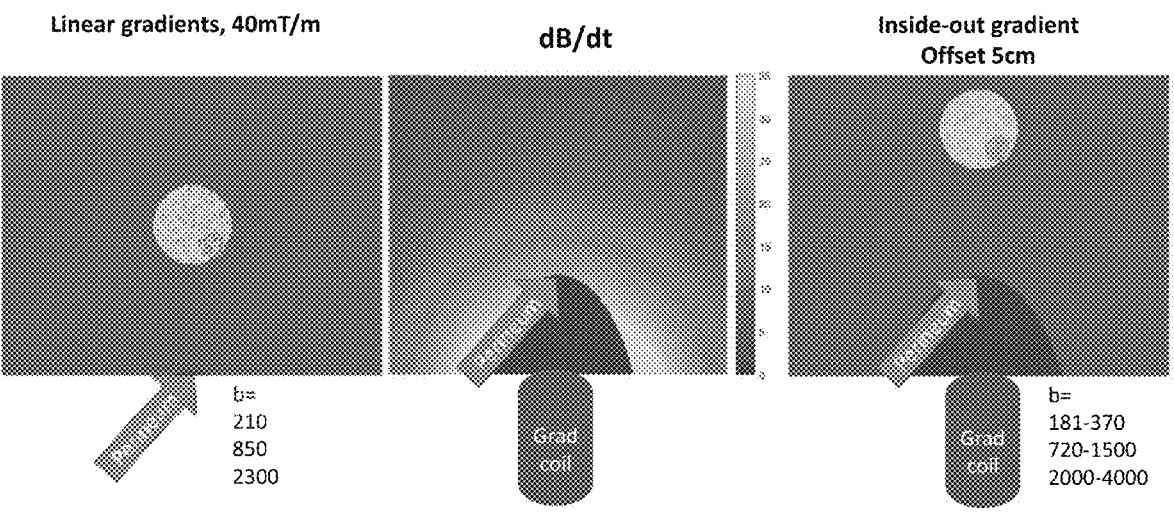

Further simulations are shown with reference to FIGS. 13A to 13I. FIG. 13A provides a simulated ADC map of a diseased prostrate that might be generated using traditional MRI techniques, FIG. 13B provides a simulated ADC map of a diseased prostrate that might be generated using the present invention, and FIG. 13C provides a simulated ADC map of the actual diseased prostrate. In an effort to demonstrate potential benefits of offsetting the magnetic resonance gradient accessory 10, FIG. 13D provides a simulated ADC map of a diseased prostrate that might be generated using traditional MRI techniques, FIG. 13E provides a simulated ADC map of a diseased prostrate that might be generated using the present magnetic resonance gradient accessory 10 in a first position, and FIG. 13F provides a simulated ADC map of a diseased prostrate that might be generated using the present magnetic resonance gradient accessory 10 in a second position shifted closer to the feet of a patient relative to the position shown in FIG. 13E. In an effort to further demonstrate potential benefits of offsetting the magnetic resonance gradient accessory 10 based upon a reduction in dB/dt within the body, FIG. 13G provides a simulated ADC map of a diseased prostrate that might be generated using traditional MRI techniques, FIG. 13H provides a simulated gradient field generated using the present magnetic resonance gradient accessory 10 in the second position shifted closer to the feet of a patient relative to the position shown in FIG. 13E, and FIG. 13I provides a simulated ADC map of a diseased prostrate that might be generated using the present magnetic resonance gradient accessory 10 in the second position shifted closer to the feet of a patient relative to the position shown in FIG. 13E.

Further to the simulations presented above, the following expression has been derived for diffusion in a nonlinear field from first principles. The derivation of this expression justifies what is seen experimentally; that is, it is sufficient to approximate the field as locally linear (within a voxel and across a diffusion length), so one can use the standard equations to derive diffusion parameters.

In particular, the simplest calculation of diffusion weighting is to consider two infinitely short gradient pulses separated by a delay T. To simplify notation and without loss of generality, we consider spin with initial location $x(t=0)=\phi(t=0)=0$, so that $\Delta x = x$ and $\Delta\phi = \phi_0$. Over the delay, the spins have localized to a Gaussian distribution of positions, $$P(x) = e^{-\frac{x^2}{\sigma^2}} \quad [1]$$

where $\sigma$ is related to the rms distance travel in time $\tau$. For linear gradients, $G_l$, after the refocusing gradient lobe, the phase of each spin depends on its positions at $t=\tau$, $$\phi(t=\tau,x) = \phi(x) = G_l \tau x = k_l x \text{ and } d\phi = k_l dx.$$

We can therefore calculate the ensemble average of magnetization M. Assuming uniform spin density, the ensemble average of M is proportional to the ensemble average of $e^{i\phi}$, which can be reformulated as an integral over x, as follows.

$$\langle \exp(i\phi) \rangle \propto \int_{-\infty}^{\infty} P(\phi) e^{i\phi} d\phi = \int_{-\infty}^{\infty} e^{-\frac{x^2}{\sigma^2}} e^{ik_l x} k_l dx = k_l \sqrt{\pi}\, \sigma e^{-\frac{k_l^2 \sigma^2}{4}}. \quad [2]$$

The product $\sigma^2 k_l^2$ reflects gradient winding, diffusion time, and diffusion rate. Thus the exponent is analogous to the product b*ADC in the well-known Stejskal-Tanner equation. Stejskal E O, Tanner J E. Spin Diffusion Measurements: Spin Echoes in the Presence of a Time-Dependent Field Gradient. Journal of Chemical Physics. 1965; 42(1): 288-292.

Using the same simplified approach for a spin in the presence of both linear and a second order nonlinear field, the difference is in the relationship between $\phi$ and x:

$$\phi(t=\tau,x) = \phi(x) = G_l \tau x + G_{nl} \tau x^2 = k_l x + k_{nl} x^2 \text{ and } d\phi = (k_l + 2 k_{nl} x) dx$$

Now the integral to be evaluated is, $$\langle \exp(i\phi) \rangle \propto \int_{-\infty}^{\infty} P(\phi) e^{i\phi} d\phi = \int_{-\infty}^{\infty} e^{-\frac{x^2}{\sigma^2}} e^{i(k_l x + k_{nl} x^2)} (k_l + 2 k_{nl} x) dx.$$

Using standard formulas, we obtain $$\langle \exp(i\phi) \rangle = k_l \left\{ \frac{\sqrt{\pi}\, \sigma}{\sqrt{1 - \sigma^2 k_{nl}}} e^{-\frac{k_l^2 \sigma^2}{4(1 - i\sigma^2 k_{nl})}} \right\} + \quad [3]$$

$$2 k_{nl} \left\{ \frac{\sqrt{\pi}\, i k_l}{2} \left( \frac{\sigma^2}{(1 - i\sigma^2 k_{nl})} \right)^{3/2} \right\} e^{-\frac{k_l^2 \sigma^2}{4(1 - i\sigma^2 k_{nl})}}.$$

Rearranging, one can obtain:

$$\langle \exp(i\phi) \rangle = k_l \sqrt{\pi}\, \sigma e^{-\frac{\sigma^2 k_l}{4(1 - i\sigma^2 k_{nl})}} \left\{ \frac{1}{\sqrt{1 - i\sigma^2 k_{nl}}} + \frac{i k_{nl} \sigma^2}{(1 - i\sigma^2 k_{nl})^{\frac{3}{2}}} \right\} \quad [4]$$

Simplifying and removing complex values from the denominators, this becomes:

$$\langle \exp(i\phi) \rangle = \quad [5]$$

$$k_l \sqrt{\pi}\, \sigma e^{-\frac{k_l^2 \sigma^2}{4(1+\sigma^4 k_{nl}^2)}} e^{\frac{i\sigma^4 k_{nl} k_l^2}{4(1+\sigma^4 k_{nl}^2)}} \left\{ \frac{\sqrt{1 + i\sigma^2 k_{nl}}}{\sqrt{1 + \sigma^4 k_{nl}^2}} + \frac{i k_{nl} \sigma^2 (1 + i\sigma^2 k_{nl})^{\frac{3}{2}}}{(1 + \sigma^4 k_{nl}^2)^{\frac{3}{2}}} \right\}$$

As expected, when $k_{nl}$ is zero this matches the linear gradient expression. More, generally, neglecting nonlinear winding will cause a slight underestimation of the effective diffusion weight, which will lead to a slight overestimation of ADCs by a scaling factor of $(1 + \sigma^4 k_{nl}^2)$. This could bias ADCs by a few percent, if not corrected. The imaginary term in the exponent indicates that nonlinear winding can also add a periodic phase shift in the signal, similar to what is observed with dephasing under a nonlinear gradient. Galiana G, Stockmann J P, Tam L, Constable R T. Spin dephasing under nonlinear gradients: Implications for imaging and field mapping. Magn Res Med 2011; 67: 1120-1126.

The complex factor in braces can alter both the magnitude and phase of the signal, in principle. However, in practice $\sigma \sim 10^{-2}$ cm and $k_{nl} \sim 10^2\text{-}10^3$ Hz/cm$^2$, over which the magnitude of this term ranges from 1 to 0.993 and its phase changes by less than 9 degrees. These corrections are highly unlikely to have clinical significance even in high precision work.

The present invention brings together major innovations and insights. The primary technical innovation of the present invention lies in abandoning the many assumptions of MRI gradients (linearity, directionality, uniformity, and rapid switching) to reinvent the hardware for maximum diffusion encoding of prostate. Gradients used for diffusion encoding are the standard gradients used for imaging. Standard principles of MR image encoding requires them to be (1) linear, (2) unidirectional, (3) uniform over a large cylindrical volume, and (4) able to switch on and off quickly. The first two requirements necessitate many magnetic field cancellations (i.e., inefficiencies), so even strong currents ultimately yield modest field gradients. Generating the field over a large volume also constrains strength, since energy requirements scale as $r^5$. Finally, designs that achieve rapid switching require low inductance, which reduces maximum amplitude, and high voltage, which limits potential for compact designs. These gradient features are so fundamental that they underpin basic concepts in MRI (e.g. k-space, Fourier sampling, and b-values), but none are required for diffusion encoding.

Physically, the diffusion weighting experienced by a voxel is related only to the local field slope at that voxel, both its magnitude and direction. Thus there is no prohibition on imposing a spatially varying diffusion weighting across a field of view. Taking that concept further, the diffusion weighting gradient can approach zero outside the anatomy of interest, opening the possibility for planar coil designs that only generate field over a small volume and are compatible with high channel receivers. Finally, since DWI applies just a few ramps per TR (repetition time), rapid switching is not critical, creating another degree of freedom. The resulting one-sided design delivers massively stronger fields (~10x) while remaining portable and compatible with different scanners.

As discussed above, in prostate MRI, DWI is considered the "dominant" or most important contrast, but the image quality of DWI is in desperate need of improvement. Huge SNR gains in DWI are possible with stronger gradients, as has already been demonstrated in tractography of brain in the Human Connectome Project. However, that approach (achieving a 10x gradient strength increase in linear gradients across a large volume) required multi-million dollar investments and challenging hardware designs which are not practical for clinical use.

In contrast, the targeted magnetic resonance gradient accessory 10 disclosed herein would be comparable in price to other anatomically specific MRI accessories, such as RF coils, while delivering a 6x gain in SNR. Its portability and ability to work with different scanners would encourage rapid and widespread adoption in clinical practice, immediately impacting patient outcomes. Therefore, the magnetic resonance gradient accessory 10 is perfectly suited to address pressing medical needs in prostate cancer diagnosis.

Finally, though the magnetic resonance gradient accessory 10 as disclosed herein is focused on prostate cancer detection, where DWI is considered the "dominant" contrast, the impact of the magnetic resonance gradient accessory 10 could reach many other areas of cancer imaging. DWI is sensitive to any increase in cellularity, making it an established tool in many diseases including cancer of the brain, liver, and breast. However, low signal and poor image quality limits its usefulness in all these applications.

For breast cancer screening in high-risk populations, reliably high quality DWI could obviate the need for decades of annual contrast administration in otherwise healthy women. Therefore, the broader impact of the magnetic resonance gradient accessory 10 is that it could drastically improve DWI for many organ systems and diseases.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A system including a magnetic resonance gradient accessory within an MRI system, comprising:
   an MRI system comprising a magnet housing, a superconducting magnet generating a magnet field $B_0$ to which a patient is subjected, shim coils, RF coils, receiver coils, magnetic gradient coils, and a patient table; and
   a magnetic resonance gradient accessory shaped and dimensioned for positioning adjacent to a body region being studied the magnetic resonance gradient accessory includes a magnetic field generating gradient coil embedded in a magnetic resonance gradient accessory housing, wherein the magnetic field generating gradient coil is electrically coupled to a gradient amplifier under control of a control system for creating local magnetic gradient fields of >400 mT/m that are critical to image generation by increasing Signal-to-Noise ratio, the magnetic resonance gradient accessory providing for diffusion encoding of a specific body region of a patient.

2. The system according to claim 1, further including measurement circuitry producing data used to reconstruct images displayed on a display.

3. The system according to claim 1, wherein the magnetic field generating gradient coil includes a set of electromagnets embedded in the magnetic resonance gradient accessory housing.

4. The system according to claim 3, wherein the magnetic field generating gradient coil comprises hollow wire conductors allowing for passage of fluid therethrough for superior heat dissipation.

5. The system according to claim 1, wherein the magnetic field generating gradient coil comprises hollow wire conductors allowing for the passage of fluid therethrough for superior heat dissipation.

6. The system according to claim 1, wherein the magnetic field generating gradient coil is centered in the magnetic resonance gradient accessory housing.

7. The system according to claim 1, wherein the magnetic resonance gradient accessory housing is secured to the patient table.

8. The system according to claim 1, further including a gradient amplifier, wherein the magnetic field generating gradient coil is electrically coupled to a gradient amplifier providing the electrical current necessary to energize the magnetic field generating gradient coil so as to distort a main magnetic field in predetermined locations to thereby create magnetic gradients.

9. The system according to claim 1, wherein the magnetic resonance gradient accessory is 10 cm long.

10. A magnetic resonance gradient accessory shaped and dimensioned for positionin adjacent to a body region being studied for use within an MRI system comprising a magnet housing, a superconducting magnet generating a magnet field $B_0$ to which a patient is subjected, shim coils, RF coils, receiver coils, magnetic gradient coils, and a patient table, the magnetic resonance gradient accessory comprising:
  a housing;
  a magnetic field generating gradient coil creating local magnetic gradient fields critical to image generation and providing for diffusion encoding of a specific body region of a patient wherein the magnetic field generating gradient coil is electrically coupled to a gradient amplifier under control of a control system creating gradients >400 mT/m that are critical to image generation by increasing Signal-to-Noise ratio.

11. The magnetic resonance gradient accessory according to claim 10, wherein the magnetic field generating gradient coil includes a set of electromagnets embedded in the magnetic resonance gradient accessory housing.

12. The magnetic resonance gradient accessory according to claim 11, wherein the magnetic field generating gradient coil comprises hollow wire conductors allowing for the passage of fluid therethrough for superior heat dissipation.

13. The magnetic resonance gradient accessory according to claim 10, wherein the magnetic field generating gradient coil comprises hollow wire conductors allowing for the passage of fluid therethrough for superior heat dissipation.

14. The magnetic resonance gradient accessory according to claim 10, wherein the magnetic field generating gradient coil is centered in the magnetic resonance gradient accessory housing.

15. The magnetic resonance gradient accessory according to claim 10, further including a gradient amplifier wherein the magnetic field generating gradient coil is electrically coupled to the gradient amplifier providing the electrical current necessary to energize the magnetic field generating gradient coil so as to distort a main magnetic field in predetermined locations to thereby creating magnetic gradients.

16. The magnetic resonance gradient accessory according to claim 10, wherein the magnetic resonance gradient accessory is 10 cm long.

* * * * *